(12) United States Patent
Igarashi et al.

(10) Patent No.: US 8,979,741 B2
(45) Date of Patent: Mar. 17, 2015

(54) ENDOSCOPIC APPARATUS

(75) Inventors: Makoto Igarashi, Sagamihara (JP); Kenji Yamazaki, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 1330 days.

(21) Appl. No.: 12/247,655

(22) Filed: Oct. 8, 2008

(65) Prior Publication Data
US 2009/0036741 A1 Feb. 5, 2009

Related U.S. Application Data

(63) Continuation of application No. PCT/JP2007/056088, filed on Mar. 23, 2007.

(30) Foreign Application Priority Data

Apr. 12, 2006 (JP) .................. 2006-110187

(51) Int. Cl.
| | |
|---|---|
| A61B 1/06 | (2006.01) |
| A61B 1/04 | (2006.01) |
| G06K 9/00 | (2006.01) |
| G02B 23/24 | (2006.01) |
| G02B 23/26 | (2006.01) |
| G02B 26/00 | (2006.01) |
| A61B 1/00 | (2006.01) |
| G02B 21/36 | (2006.01) |

(52) U.S. Cl.
CPC .......... *G02B 23/2484* (2013.01); *A61B 1/0638* (2013.01); *G02B 23/2469* (2013.01);
(Continued)

(58) Field of Classification Search
CPC .. A61B 1/00004; A61B 1/00009; A61B 1/04; A61B 1/043; A61B 1/05; A61B 1/00186; A61B 1/06; A61B 1/38; A61B 1/0646; A61B 1/0653; A61B 1/0661

USPC .......... 348/68–70, 577, 582, 599, 663; 600/109, 160, 178, 180, 181, 476

See application file for complete search history.

(56) References Cited

U.S. PATENT DOCUMENTS

| | | | | |
|---|---|---|---|---|
| 5,512,940 | A | * | 4/1996 | Takasugi et al. ................ 348/71 |
| 6,889,075 | B2 | * | 5/2005 | Marchitto et al. ............ 600/473 |

(Continued)

FOREIGN PATENT DOCUMENTS

| | | |
|---|---|---|
| EP | 1 302 152 A1 | 4/2003 |
| JP | 2002-034908 | 2/2002 |

(Continued)

OTHER PUBLICATIONS

Extended Supplementary European Search Report dated Feb. 26, 2013 from related application EP 07739529.1-1660.

*Primary Examiner* — Anhtuan T Nguyen
*Assistant Examiner* — William Chou
(74) *Attorney, Agent, or Firm* — Scully, Scott, Murphy & Presser, PC (57) ABSTRACT

An endoscopic apparatus according to the invention has an illumination unit capable of emitting to a subject first narrow band light having a wavelength band in a blue region and second narrow band light having a wavelength band in a green region, an image pickup unit which picks up a first subject image when the subject in the living body is illuminated with the first narrow band light, and picks up a second subject image when the subject in the living body is illuminated with the second narrow band light, a storage unit which stores the first subject image as a green component and a blue component, and stores the second subject image as a red component and a blue component, and a color tone conversion unit which performs predetermined color conversion processing to form an image of a predetermined object as an image having a predetermined first color.

15 Claims, 5 Drawing Sheets

(52) U.S. Cl.
CPC .............. *G02B23/26* (2013.01); *G02B 26/008* (2013.01); *A61B 1/00009* (2013.01); *A61B 1/0005* (2013.01); *A61B 1/0653* (2013.01); *A61B 1/063* (2013.01); *A61B 1/0646* (2013.01); *G02B 21/365* (2013.01)
USPC ........... 600/160; 600/109; 600/178; 600/181; 382/128

(56) References Cited

U.S. PATENT DOCUMENTS

| 7,704,206 | B2 * | 4/2010 | Suzuki et al. ................. 600/178 |
| 2004/0215060 | A1 * | 10/2004 | Ueno et al. .................... 600/160 |
| 2004/0263643 | A1 | 12/2004 | Imaizumi et al. |
| 2006/0178565 | A1 * | 8/2006 | Matsui et al. ................. 600/160 |
| 2006/0198551 | A1 * | 9/2006 | Abe et al. ...................... 382/128 |
| 2006/0211915 | A1 * | 9/2006 | Takeuchi et al. .............. 600/109 |
| 2007/0100207 | A1 * | 5/2007 | Ueno et al. .................... 600/160 |
| 2009/0023991 | A1 * | 1/2009 | Gono et al. .................... 600/109 |
| 2009/0091614 | A1 * | 4/2009 | Gono et al. .................... 348/68 |

FOREIGN PATENT DOCUMENTS

| JP | 2002-095635 | 4/2002 |
| WO | WO 02/07588 A1 | 1/2002 |
| WO | WO 2005/046248 A1 | 5/2005 |
| WO | WO 2006/025334 A1 | 3/2006 |

* cited by examiner

ENDOSCOPIC APPARATUS

CROSS REFERENCE TO RELATED APPLICATION

This application is a continuation application of PCT/JP2007/056088 filed on Mar. 23, 2007 and claims benefit of Japanese Application No. 2006-110187 filed in Japan on Apr. 12, 2006, the entire contents of which are incorporated herein by this reference.

BACKGROUND OF THE INVENTION

1. Field of the Invention

The present invention relates to an endoscopic apparatus and, more particularly, to an endoscopic apparatus capable of imaging an internal portion of a living body by means of a narrow band light.

2. Description of the Related Art

Endoscopic apparatuses having an endoscope, a light source device and other components have been widely used in the field of medical treatment or the like. In particular, endoscopic apparatuses in the field of medical treatment are applied mainly to uses in which an operator or the like performs imaging or the like of an internal portion of a living body.

Instances of imaging with an endoscopic apparatus generally known in the field of medical treatment include normal imaging that is performed by irradiating a subject in a living body with white light, and that enables obtaining generally the same image of the subject as one observed with the naked eye, and imaging with a narrow band light (narrow band imaging (NBI)) that is performed by irradiating the subject with narrow band light having a band narrower than that of illumination light in the normal imaging, and that thereby enables obtaining an image in which blood vessels and other portions in a mucosal surface layer in a living body are emphasized in comparison with the normal imaging.

An endoscopic apparatus proposed in Japanese Patent Application Laid-Open Publication No. 2002-095635 is configured of a light source device provided with a filter having discrete spectral characteristics for outputting a narrow band illumination light, and an endoscope for picking up an image of a subject illuminated with the illumination light. The endoscopic system proposed in Japanese Patent Application Laid-Open Publication No. 2002-095635 has the above-described configuration and is therefore capable of narrow band imaging of the subject.

SUMMARY OF THE INVENTION

An endoscopic apparatus according to a first aspect of the present invention includes an illumination unit capable of emitting to a subject in a living body first narrow band light having a wavelength band in a blue region and second narrow band light having a wavelength band in a green region, an image pickup unit of picking up a first subject image when the subject in the living body is illuminated with the first narrow band light, and picking up a second subject image when the subject in the living body is illuminated with the second narrow band light, a storage unit of storing the first subject image as a green component and a blue component, and storing the second subject image as a red component and a blue component, and a color tone conversion unit of performing predetermined color conversion processing on the red component, the green component and the blue component, to form an image of a predetermined object other than living tissues picked up as the first subject image and the second subject image as an image having a predetermined first color other than red.

An endoscopic apparatus of a second aspect of the present invention is the endoscopic apparatus according to the first aspect, wherein the predetermined object comprises at least one of a residue, bile and intestinal juice existing in the living body.

An endoscopic apparatus of a third aspect of the present invention is the endoscopic apparatus according to the first aspect, wherein the color tone conversion unit performs processing, as the predetermined color conversion processing, on the basis of the second subject image accumulated as the red component, the first subject image accumulated as the green component and the second subject image accumulated as the blue component so that the luminance value of the red component and the luminance value of the blue component in the image of the predetermined object are substantially equal to each other.

An endoscopic apparatus of a fourth aspect of the present invention is the endoscopic apparatus according to the second aspect, wherein the color tone conversion unit performs processing, as the predetermined color conversion processing, on the basis of the second subject image accumulated as the red component, the first subject image accumulated as the green component and the second subject image accumulated as the blue component so that the luminance value of the red component and the luminance value of the blue component in the image of the predetermined object are substantially equal to each other.

An endoscopic apparatus of a fifth aspect of the present invention is the endoscopic apparatus according to the first aspect, wherein the predetermined first color is magenta.

An endoscopic apparatus of a sixth aspect of the present invention is the endoscopic apparatus according to the second aspect, wherein the predetermined first color is magenta.

An endoscopic apparatus of a seventh aspect of the present invention is the endoscopic apparatus according to the third aspect, wherein the predetermined first color is magenta.

An endoscopic apparatus of an eighth aspect of the present invention is the endoscopic apparatus according to fourth aspect, wherein the predetermined first color is magenta.

An endoscopic apparatus of a ninth aspect of the present invention is the endoscopic apparatus according to the first aspect, wherein the color tone conversion unit further performs processing, as the predetermined color conversion processing, on the basis of the second subject image accumulated as the red component, the first subject image accumulated as the green component and the first and second subject images accumulated as the blue component, to form an image of a local portion picked up as the first subject image and the second subject image and having halation therein into as an image having a predetermined second color.

An endoscopic apparatus of a tenth aspect of the present invention is the endoscopic apparatus according to the second aspect, wherein the color tone conversion unit further performs processing, as the predetermined color conversion processing, on the basis of the second subject image accumulated as the red component, the first subject image accumulated as the green component and the first and second subject images accumulated as the blue component, to form an image of a local portion picked up as the first subject image and the second subject image and having halation therein as an image having a predetermined second color.

An endoscopic apparatus of an eleventh aspect of the present invention is the endoscopic apparatus according to the ninth aspect, wherein the predetermined second color is white.

An endoscopic apparatus of a twelfth aspect of the present invention is the endoscopic apparatus according to the tenth aspect, wherein the predetermined second color is white.

An endoscopic apparatus of a thirteenth aspect of the present invention is the endoscopic apparatus according to the first aspect, wherein the illumination unit successively emits the first narrow band light and the second narrow band light to the subject.

An endoscopic apparatus of a fourteenth aspect of the present invention is the endoscopic apparatus according to the second aspect, wherein the illumination unit successively emits the first narrow band light and the second narrow band light to the subject.

An endoscopic apparatus of a fifteenth aspect of the present invention is the endoscopic apparatus according to the third aspect, wherein the illumination unit successively emits the first narrow band light and the second narrow band light to the subject.

An endoscopic apparatus of a sixteenth aspect of the present invention is the endoscopic apparatus according to the fourth aspect, wherein the illumination unit successively emits the first narrow band light and the second narrow band light to the subject.

An endoscopic apparatus of a seventeenth aspect of the present invention is the endoscopic apparatus according to the fifth aspect, wherein the illumination unit successively emits the first narrow band light and the second narrow band light to the subject.

An endoscopic apparatus of an eighteenth aspect of the present invention is the endoscopic apparatus according to the sixth aspect, wherein the illumination unit successively emits the first narrow band light and the second narrow band light to the subject.

An endoscopic apparatus of a nineteenth aspect of the present invention is the endoscopic apparatus according to the seventh aspect, wherein the illumination unit successively emits the first narrow band light and the second narrow band light to the subject.

An endoscopic apparatus of a twentieth aspect of the present invention is the endoscopic apparatus according to the eighth aspect, wherein the illumination unit successively emits the first narrow band light and the second narrow band light to the subject.

An endoscopic apparatus of a twenty-first aspect of the present invention is the endoscopic apparatus according to the ninth aspect, wherein the illumination unit successively emits the first narrow band light and the second narrow band light to the subject.

An endoscopic apparatus of a twenty-second aspect of the present invention is the endoscopic apparatus according to the tenth aspect, wherein the illumination unit successively emits the first narrow band light and the second narrow band light to the subject.

An endoscopic apparatus of a twenty-third aspect of the present invention is the endoscopic apparatus according to the eleventh aspect, wherein the illumination unit successively emits the first narrow band light and the second narrow band light to the subject.

An endoscopic apparatus of a twenty-fourth aspect of the present invention is the endoscopic apparatus according to the twelfth aspect, wherein the illumination unit successively emits the first narrow band light and the second narrow band light to the subject.

An endoscopic apparatus of a twenty-fifth aspect of the present invention is the endoscopic apparatus according to the first aspect, wherein the illumination unit simultaneously emits the first narrow band light and the second narrow band light to the subject.

An endoscopic apparatus of a twenty-sixth aspect of the present invention is the endoscopic apparatus according to the second aspect, wherein the illumination unit simultaneously emits the first narrow band light and the second narrow band light to the subject.

An endoscopic apparatus of a twenty-seventh aspect of the present invention is the endoscopic apparatus according to the third aspect, wherein the illumination unit simultaneously emits the first narrow band light and the second narrow band light to the subject.

An endoscopic apparatus of a twenty-eighth aspect of the present invention is the endoscopic apparatus according to the fourth aspect, wherein the illumination unit simultaneously emits the first narrow band light and the second narrow band light to the subject.

An endoscopic apparatus of a twenty-ninth aspect of the present invention is the endoscopic apparatus according to the fifth aspect, wherein the illumination unit simultaneously emits the first narrow band light and the second narrow band light to the subject.

An endoscopic apparatus of a thirtieth aspect of the present invention is the endoscopic apparatus according to the sixth aspect, wherein the illumination unit simultaneously emits the first narrow band light and the second narrow band light to the subject.

An endoscopic apparatus of a thirty-first aspect of the present invention is the endoscopic apparatus according to the seventh aspect, wherein the illumination unit simultaneously emits the first narrow band light and the second narrow band light to the subject.

An endoscopic apparatus of a thirty-second aspect of the present invention is the endoscopic apparatus according to the eighth aspect, wherein the illumination unit simultaneously emits the first narrow band light and the second narrow band light to the subject.

An endoscopic apparatus of a thirty-third aspect of the present invention is the endoscopic apparatus according to the ninth aspect, wherein the illumination unit simultaneously emits the first narrow band light and the second narrow band light to the subject.

An endoscopic apparatus of a thirty-fourth aspect of the present invention is the endoscopic apparatus according to the tenth aspect, wherein the illumination unit simultaneously emits the first narrow band light and the second narrow band light to the subject.

An endoscopic apparatus of a thirty-fifth aspect of the present invention is the endoscopic apparatus according to the eleventh aspect, wherein the illumination unit simultaneously emits the first narrow band light and the second narrow band light to the subject.

An endoscopic apparatus of a thirty-sixth aspect of the present invention is the endoscopic apparatus according to the twelfth aspect, wherein the illumination unit simultaneously emits the first narrow band light and the second narrow band light to the subject.

DESCRIPTION OF THE PREFERRED EMBODIMENT(S)

(First Embodiment)

Figure 1:
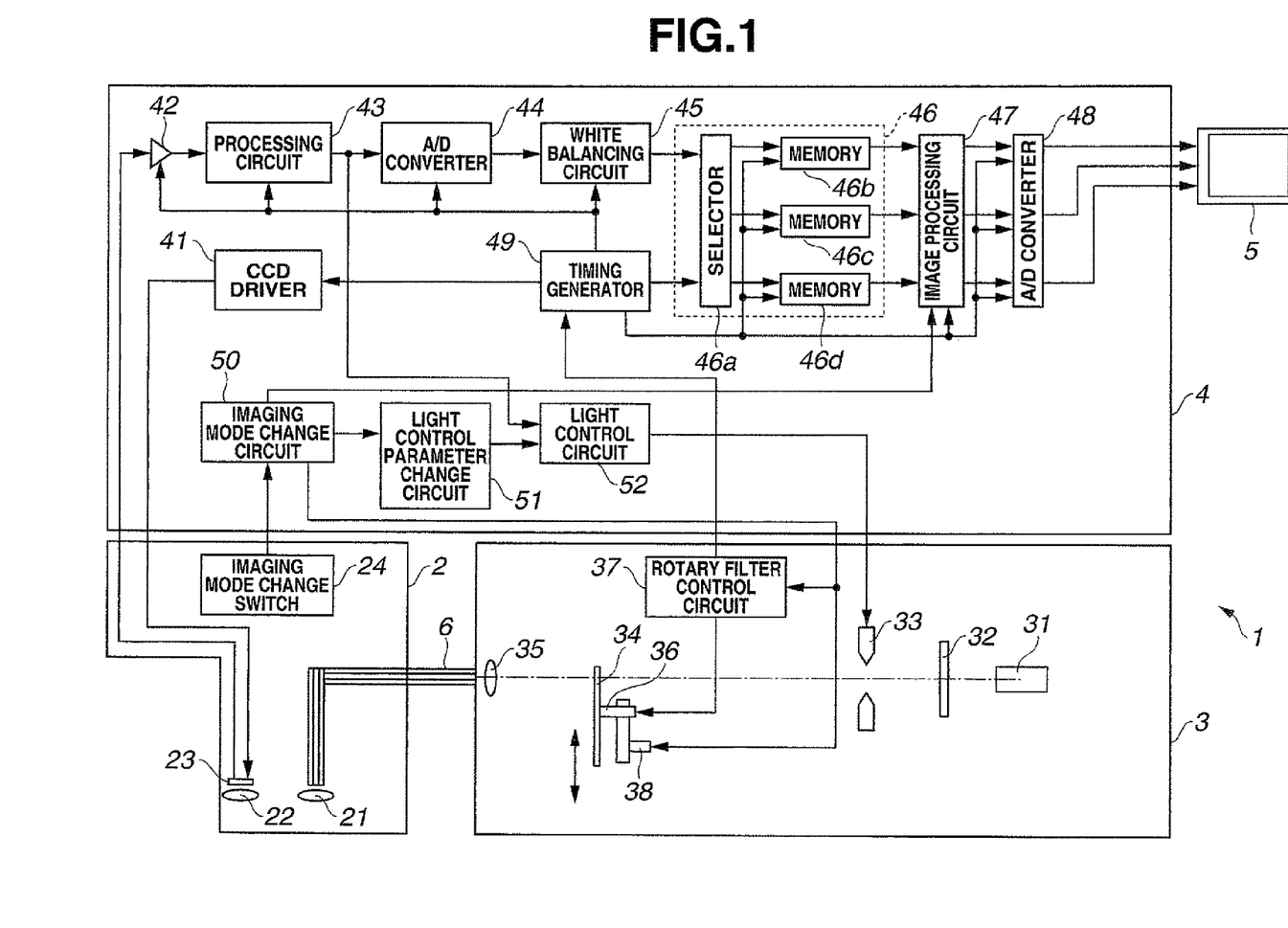
FIG. 1 is a diagram showing an example of a configuration of essential components of an endoscopic apparatus according to a first embodiment.
Figure 2:
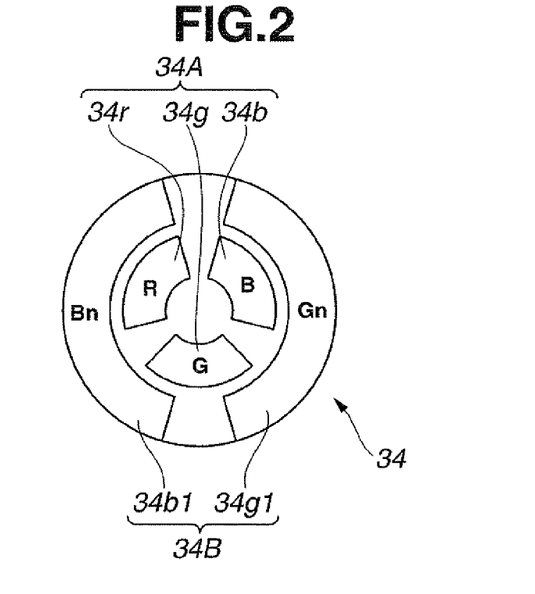
FIG. 2 is a diagram showing an example of a configuration of a rotary filter in the endoscopic apparatus shown in FIG. 1.
Figure 3:
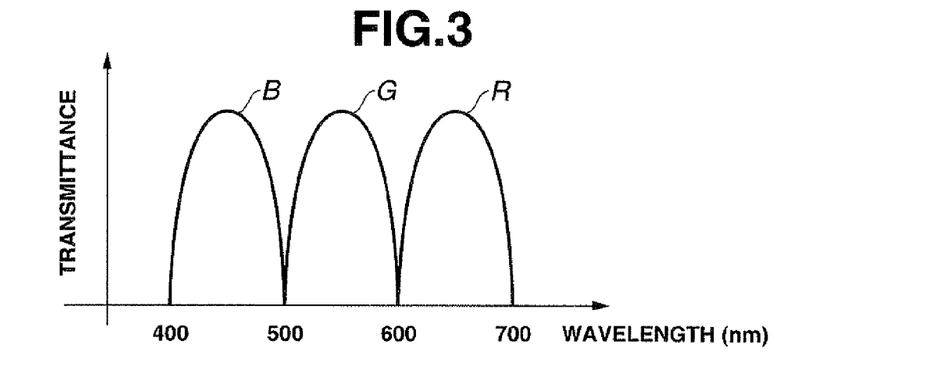
FIG. 3 is a diagram showing an example of transmission characteristics of a first group of filters in the rotary filter shown in FIG. 2.
Figure 4:
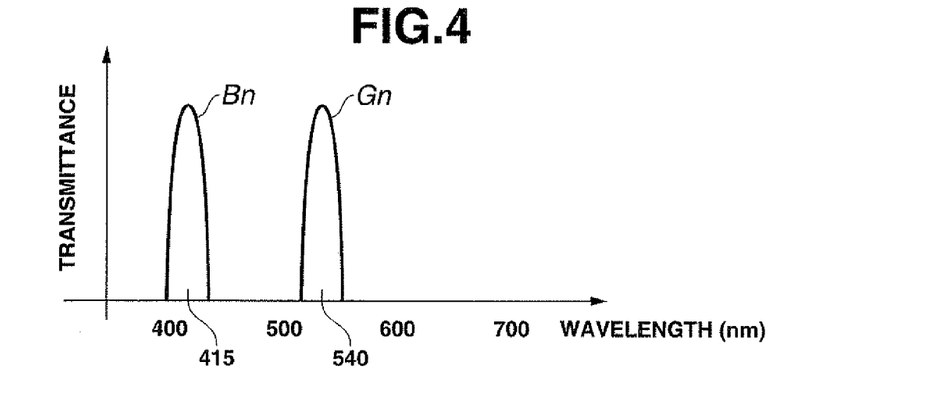
FIG. 4 is a diagram showing an example of transmission characteristics of a second group of filters in the rotary filter shown in FIG. 2.
Figure 5:
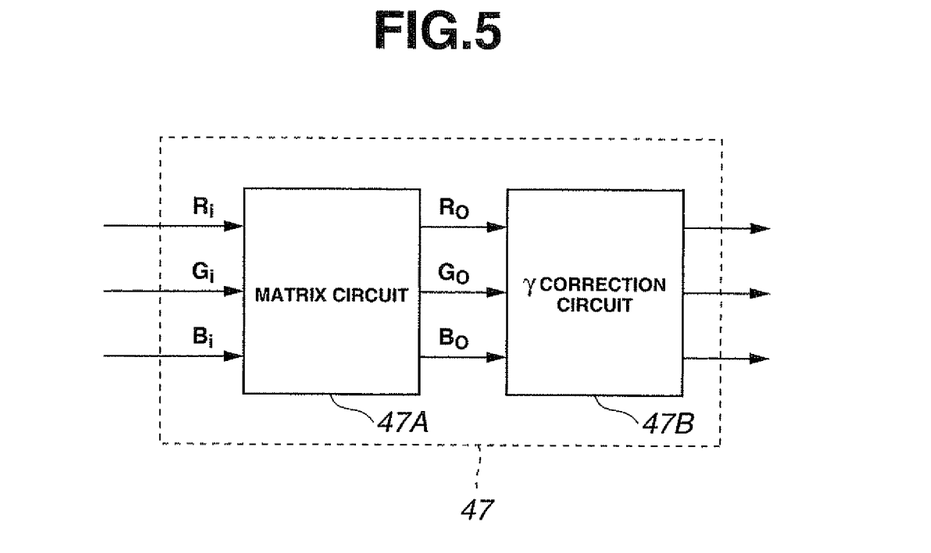
FIG. 5 is a diagram showing an example of a configuration of an image processing circuit in the endoscopic apparatus shown in FIG. 1.
Figure 6:
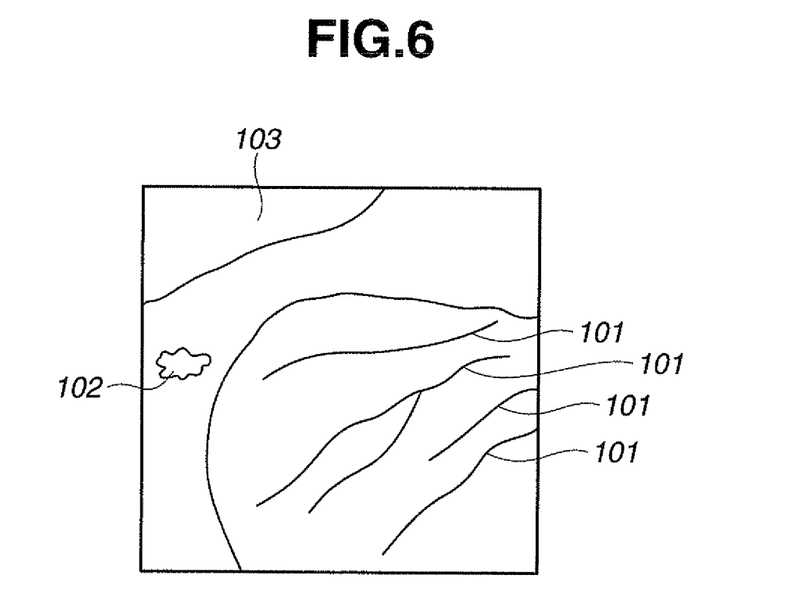
FIG. 6 is a diagram showing an example of an image of a subject in a narrow band imaging mode obtained by imaging using the endoscopic apparatus shown in FIG. 1.

FIGS. 1 to 6 relate to a first embodiment of the present invention. FIG. 1 is a diagram showing an example of a configuration of essential components of an endoscopic apparatus according to the first embodiment. FIG. 2 is a diagram showing an example of a configuration of a rotary filter in the endoscopic apparatus shown in FIG. 1. FIG. 3 is a diagram showing an example of transmission characteristics of a first group of filters in the rotary filter shown in FIG. 2. FIG. 4 is a diagram showing an example of transmission characteristics of a second group of filters in the rotary filter shown in FIG. 2. FIG. 5 is a diagram showing an example of a configuration of an image processing circuit in the endoscopic apparatus shown in FIG. 1. FIG. 6 is a diagram showing an example of an image of a subject in a narrow band imaging mode obtained by imaging using the endoscopic apparatus shown in FIG. 1.

As shown in FIG. 1, the endoscopic apparatus 1 according to the first embodiment is configured essentially of an endoscope 2 which can be inserted in a living body, which picks up an image of a subject such as a living tissue existing in the living body, and which outputs an image of the living tissue as an image pickup signal, a light source device 3 which supplies illumination light for illuminating a subject to the endoscope 2 through a light guide 6, a video processor 4 which performs signal processing according to the image pickup signal outputted from the endoscope 2 and outputs as a video signal the image pickup signal after the signal processing, and a monitor 5 which displays the image of a subject picked up by the endoscope 2 on the basis of the video signal outputted from the video processor 4.

The endoscope 2 is configured of an illumination optical system 21 through which illumination light supplied from the light source device 3 and transmitted through the light guide 6 is emitted, an objective optical system 22 which forms an image of a subject illuminated with illumination light emitted from the illumination optical system 21, a CCD (charge-coupled device) 23 disposed at the image forming position of the objective optical system 22, and an imaging mode change switch 24 which outputs an imaging mode change command signal to the video processor 4 to change imaging modes of the endoscopic apparatus 1.

The CCD 23 as an image pickup unit picks up images of a subject illuminated with illumination light successively emitted from the illumination optical system 21 and outputs the images of the subject as image pickup signals.

The imaging mode change switch 24 can be operated by an operator or the like to select one of imaging modes of the endoscopic apparatus 1: a normal imaging mode in which generally the same image of a subject as the image of the subject observed with the naked eye can be obtained, and a narrow band imaging mode in which images in which blood vessels and other portions in a mucosal surface layer in a living body are emphasized can be obtained.

The light source device 3 as an illumination unit has a lamp 31 which is constituted by a xenon lamp or the like, and which emits white light, a heat ray cut filter 32 which blocks heat rays in the white light emitted from the lamp 31, a diaphragm device 33 which controls the quantity of white light passing through the heat ray cut filter on the basis of a diaphragm control signal outputted from the video processor 4, a rotary filter 34 which changes white light passing through the diaphragm device 33 into surface-sequential illumination light, and a collective optical system 35 which collects surface-sequential illumination light passing through the rotary filter 34 and supplies the collected surface-sequential illumination light to the light guide 6.

As shown in FIG. 2, the rotary filter 34 is configured in the form of a disk having an axis of rotation at its center, and has a first filter group 34A provided with a plurality of filters formed along a circumferential direction at an inner peripheral position and a second filter group 34B provided with a plurality of filters formed along a circumferential direction at an outer peripheral position.

The first filter group 34A is configured of an R filter 34r which transmits light having a wavelength band in a red region, a G filter 34g which transmits light having a wavelength band in a green region, and a B filter 34b which transmits light having a wavelength band in a blue region, the filters 34r, 34g, and 34b being provided in the circumferential direction at the inner peripheral position in the rotary filter 34.

The R filter 34r has such a configuration as to transmit, for example, light from 600 nm to 700 nm as light having a wavelength band in a red region, as shown in FIG. 3. The G filter 34g has such a configuration as to transmit, for example, light from 500 nm to 600 nm as light having a wavelength band in a green region, as shown in FIG. 3. The B filter 34b has such a configuration as to transmit, for example, light from 400 mm to 500 nm as light having a wavelength band in a blue region, as shown in FIG. 3.

The second filter group 34B is configured of a Bn filter 34b1 which transmits narrow band light in a blue region, and a Gn filter 34g1 which transmits narrow band light in a green region, the filters 34b1 and 34g1 being provided in the circumferential direction at the outer peripheral position in the rotary filter 34.

The Bn filter 34b1 has such a configuration as to transmit, for example, light of 415 nm ±15 nm as narrow band light in a blue region, as shown in FIG. 4. The Gn filter 34g1 has such a configuration as to transmit, for example, light of 540 nm ±15 nm as narrow band light in a green region, as shown in FIG. 4.

In the first embodiment, the second filter group 34B is not limited to the one configured only of the Bn filter 34b1 and the Gn filter 34g1, and may alternatively be configured of, for example, the above-described two filters and another filter which transmits narrow band light in a red region.

The light source device 3 further has a rotary filter motor 36 which rotatively drives the rotary filter 34, a rotary filter control circuit 37 which controls the rotative drive of the rotary filter motor 36 on the basis of an imaging mode change signal outputted from the video processor 4, and which outputs a sync signal synchronized with the rotation of the rotary filter 34 to the video processor 4, and a filter change motor 38 which drives on the basis of the imaging mode change signal outputted from the video processor 4.

The filter change motor 38 places on the optical path of the lamp 31 one of the first filter group 34A and the second filter group 34B provided in the rotary filter 34, on the basis of the imaging mode change signal outputted from the video processor 4.

When, for example, the first filter group 34A is placed on the optical path of the lamp 31, the above-described configurations of the portions of the light source device 3 enable white light passing through the R filter 34r, the G filter 34g and the B filter 34b to be collected as surface-sequential illumination light formed of R (red) light, C (green) light and B (blue) light by the collective optical system 35 and thereafter supplied to the light guide 6. When, for example, the second filter group 34B is placed on the optical path of the lamp 31, white light passing through the Bn filter 34b1 and the Gn filter 34g1 is collected as surface-sequential illumination light formed of narrow band light in a blue region (hereinafter referred to as Bn light) and narrow band light in a green region (hereinafter referred to as Gn light) by the collective optical system 35 and thereafter supplied to the light guide 6.

The video processor 4 has a CCD driver 41 which drives the CCD 23 provided in the endoscope 2, an amplifier 42 which amplifies the image pickup signal outputted from the CCD 23, a processing circuit 43 which performs processing including correlative double sampling and noise removal on the image pickup signal outputted from the amplifier 42, an A/D converter 44 which converts the image pickup signal outputted from the processing circuit 43 into a digital image signal, and a white balancing circuit 45 which performs white balancing processing on the image signal outputted from the A/D converter 44.

The video processor 4 also has a synchronization circuit 46 which temporarily stores and synchronizes image signals successively outputted from the white balancing circuit 45, an image processing circuit 47 which reads out a one-frame image signal from the image signals stored in the synchronization circuit 46 and performs matrix conversion processing and gamma correction processing on the one-frame image signal, a D/A converter 48 which converts the image signal outputted from the image processing circuit 47 into an analog video signal and outputs this signal, and a timing generator 49 which outputs a timing signal to each of the above-described sections of the video processor 4 according to the sync signal outputted from the rotary filter control circuit 37 of the light source device 3.

The synchronization circuit 46 is constituted of a selector 46a and memories 46b, 46c, and 46d.

The selector 46a successively outputs to the memories 46b, 46c, and 46d image signals outputted from the white balancing circuit 45 on the basis of the timing signal outputted from the timing generator 49.

In the memories 46b, 46c, and 46d as a storage unit, the memory 46b is configured as an R-channel memory, the memory 46c as a G-channel memory, and the memory 46d as a B-channel memory. That is, the image signal inputted to the memory 46b is accumulated as a red component; the image signal inputted to the memory 46c as a green component; and the image signal inputted to the memory 46d as a blue component.

The memories 46b, 46c, and 46d temporarily store and synchronize the image signals outputted from the selector 46a on the basis of the timing signal outputted from the timing generator 49.

The image processing circuit 47 is constituted of a matrix circuit 47A, and a γ correction circuit 47B, as shown in FIG. 5. The image processing circuit 47 performs image processing according to the normal imaging mode or the narrow band imaging mode on the basis of the imaging mode change signal outputted from an imaging mode change circuit 50 described below.

The matrix circuit 47A as a color tone conversion unit performs matrix conversion processing described below on the one-frame image signal read out from the synchronization circuit 46 and formed of red, green and blue components to convert the color of the subject in the image signal into a color according to the imaging mode, and thereafter outputs the image signal.

The γ correction circuit 47B performs γ correction processing on the image signal having undergone matrix conversion processing by the matrix circuit 47A, and outputs the processed image signal.

The video processor 4 further has the imaging mode change circuit 50, a light control parameter change circuit 51 and a light control circuit 52.

The imaging mode change circuit 50 outputs, on the basis of the imaging mode change command signal outputted from the endoscope 2, the imaging mode change signal to make each section of the light source device 3 and the video processor 4 perform the operation according to the imaging mode.

The light control parameter change circuit 51 outputs a light control parameter according to the imaging mode on the basis of the imaging mode change signal outputted from the imaging mode change circuit 50.

The light control circuit 52 outputs a diaphragm control signal for brightness control according to the imaging mode to the diaphragm device 33 on the basis of the light control parameter outputted by the light control parameter change circuit 51 and the image pickup signal outputted from the processing circuit 43.

Next, the operation of the endoscopic apparatus 1 will be described.

An operator or the like first powers on the components of the endoscopic apparatus 1, i.e., the endoscope 2, the light source device 3, the video processor 4 and the monitor 5 to activate the components. Note that, it is assumed that in the activated state the endoscope 2, the light source device 3 and the video processor 4 are set in the normal imaging mode.

In the case where the video processor 4 is set in the normal imaging mode, the imaging mode change circuit 50 outputs the imaging mode change signal to the filter change motor 38 on the basis of the imaging mode change command signal outputted from the imaging mode change switch 24 so that the first filter group 34A in the rotary filter 34 is placed on the optical path of the lamp 31. The imaging mode change circuit 50 also outputs the imaging mode change signal to the light control parameter change circuit 51 on the basis of the imaging mode change command signal outputted from the imaging mode change switch 24 so that a light control parameter suitable for the normal imaging mode is outputted. Further, the imaging mode change circuit 50 outputs the imaging mode change signal to the rotary filter control circuit 37 on the basis of the imaging mode change command signal outputted from the imaging mode change switch 24 so that the rotary filter 34 is rotatively driven at a rotational speed suitable for the normal imaging mode.

The light control parameter change circuit 51 then outputs the light control parameter suitable for the normal imaging mode to the light control circuit 52 on the basis of the imaging mode change signal.

The light control circuit 52 outputs the diaphragm control signal to the diaphragm device 33 on the basis of the light control parameter outputted from the light control parameter change circuit 51 so that a quantity of illumination light suitable for the normal imaging mode is supplied by the light source device 3.

The light source device 3 supplies surface-sequential illumination light formed of R light, G light and B light to the light guide 6 based on the imaging mode change signals respectively inputted to the diaphragm device 33, the rotary filter control circuit 37 and the filter change motor 38. Also, the rotary filter control circuit 37 of the light source device 3 outputs the sync signal synchronized with the rotation of the rotary filter 34 to the video processor 4.

The surface-sequential illumination light formed of R light, G light and B light is emitted to a subject through the light guide 6 and the illumination optical system 21.

An image of the subject illuminated with the surface-sequential illumination light formed of R light, G light and B light is formed by the objective optical system 22, picked up by the CCD 23 and then outputted as an image pickup signal to the video processor 4.

The image pickup signal outputted to the video processor 4 is amplified by the amplifier 42, undergoes processing including correlative double sampling and noise removal performed by the processing circuit 43, and is converted into a digital image signal by the A/D converter 44. This digital image signal undergoes white balancing processing performed by the white balancing circuit 45. A one-frame image signal is obtained from the digital image signal by synchronization in the synchronization circuit 46 and is read to the image processing circuit 47. Next that, in the normal imaging mode, the image signal for the R light subject image is accumulated as a red component in the memory 46b, the image signal for the G light subject image is accumulated as a green component in the memory 46c, and the image signal for the B light subject image is accumulated as a blue component in the memory 46d.

When detecting the setting of the video processor 4 in the normal imaging mode on the basis of the imaging mode change signal outputted from the imaging mode change circuit 50, the image processing circuit 47 performs only γ correction processing in the γ correction circuit 47B on the image signal read from the synchronization circuit 46 without performing matrix conversion processing, described below, in the matrix circuit 47A, and outputs the image signal having undergone the γ correction.

The image signal outputted from the image processing circuit 47 is converted into an analog video signal by the D/A converter 48 and thereafter outputted to the monitor 5.

As a result of the above-described processing performed in the video processor 4, an image of the subject which is substantially the same as the image of the subject imaged with the naked eye, is displayed on the monitor 5 as an image of the subject in the normal imaging mode.

The operator or the like thereafter operates and moves the endoscope 2 so that the desired subject in a living body is positioned within the field of view of the objective optical system 22 and at a position at which it is illuminated with illumination light emitted from the illumination optical system 21. In this state, the operator or the like changes the imaging mode of the endoscopic apparatus 1 from the normal imaging mode to the narrow band imaging mode by operating the imaging mode change switch 24.

When the video processor 4 is set in the narrow band imaging mode, the imaging mode change circuit 50 outputs the imaging mode change signal to the filter change motor 38 on the basis of the imaging mode change command signal outputted from the imaging mode change switch 24 so that the second filter group 34B in the rotary filter 34 is placed on the optical path of the lamp 31. The imaging mode change circuit 50 also outputs the imaging mode change signal to the light control parameter change circuit 51 on the basis of the imaging mode change command signal outputted from the imaging mode change switch 24 so that a light control parameter suitable for the narrow band imaging mode is outputted. Further, the imaging mode change circuit 50 outputs the imaging mode change signal to the rotary filter control circuit 37 on the basis of the imaging mode change command signal outputted from the imaging mode change switch 24 so that the rotary filter 34 is rotatively driven at a rotational speed suitable for the narrow band imaging mode.

The light control parameter change circuit 51 then outputs the light control parameter suitable for the narrow band imaging mode to the light control circuit 52 on the basis of the imaging mode change signal.

The light control circuit 52 outputs the diaphragm control signal to the diaphragm device 33 on the basis of the light control parameter outputted from the light control parameter change circuit 51 so that a quantity of illumination light suitable for the narrow band imaging mode is supplied by the light source device 3.

The light source device 3 supplies surface-sequential illumination light formed of Gn light and Bn light to the light guide 6 based on the imaging mode change signals respectively inputted to the diaphragm device 33, the rotary filter control circuit 37 and the filter change motor 38. Also, the rotary filter control circuit 37 of the light source device 3 outputs the sync signal synchronized with the rotation of the rotary filter 34 to the video processor 4.

The surface-sequential illumination light formed of Gn light and Bn light is emitted to the subject through the light guide 6 and the illumination optical system 21.

An image of the subject illuminated with the surface-sequential illumination light formed of Gn light and Bn light is formed by the objective optical system 22, picked up by the CCD 23, and then outputted as an image pickup signal to the video processor 4. That is, the CCD 23 picks up a first subject image when the subject is illuminated with Bn light, picks up a second subject image when the subject is illuminated with Gn light, and outputs each subject image as an image pickup signal.

The image pickup signal outputted to the video processor 4 is amplified by the amplifier 42, undergoes processing including correlative double sampling and noise removal performed by the processing circuit 43, and is converted into a digital image signal by the A/D converter 44. This digital image signal undergoes white balancing processing performed by the white balancing circuit 45. A one-frame image signal is obtained from the digital image signal by synchronization in the synchronization circuit 46 and is read to the image processing circuit 47. In the narrow band imaging mode, the selector 46a outputs a $G_t$ signal, which is an image signal for the image of the subject illuminated with Gn light, to the memories 46b and 46d, and outputs a $B_t$ signal, which is an image signal for the image of the subject illuminated with Bn light, to the memories 46c and 46d.

When the image processing circuit 47 detects the setting of the video processor 4 in the narrow band imaging mode on the basis of the imaging mode change signal outputted from the imaging mode change circuit 50, the image processing circuit 47 performs matrix conversion processing as predetermined color conversion processing on each image signal read from the synchronization circuit 46 in the matrix circuit 47A.

The matrix circuit 47A performs matrix conversion based on the expression (1) shown below, on each of the $G_i$ and $B_i$ signals read from the memories in the synchronization circuit 46 to output an $R_o$ signal, a $G_o$ signal and a $B_o$ signal as red, green and blue components therefrom.

$$\begin{pmatrix} R_o \\ G_o \\ B_o \end{pmatrix} = \begin{pmatrix} k_1 & 0 \\ 0 & k_2 \\ k_3 & 0 \end{pmatrix} \begin{pmatrix} Gi \\ Bi \end{pmatrix} \quad (1)$$

More specifically, the matrix circuit 47A performs matrix conversion processing based on the expression (1) shown above by multiplying the luminance value of the $G_i$ signal read from the memory 46b by $k_1$ to obtain a signal and outputs this signal as an $R_o$ signal which is a red component after the matrix conversion processing.

Also, the matrix circuit 47A performs matrix conversion processing based on the expression (1) shown above by multiplying the luminance value of the $B_i$ signal read from the memory 46c by $k_2$ to obtain a signal and outputs this signal as a $G_o$ signal which is a green component after the matrix conversion processing.

Further, the matrix circuit 47A performs matrix conversion processing based on the expression (1) shown above by multiplying the luminance value of the $G_i$ signal read from the memory 46d by $k_3$ to obtain a signal and outputs this signal as a $B_o$ signal which is a blue component after the matrix conversion processing.

In expression (1), it is noted that the constant $k_3$ is a value smaller than either of the constant $k_1$ and the constant $k_2$. More specifically, it is noted that the values of the constant $k_1$, the constant $k_2$ and the constant $k_3$ satisfy, for example, a magnitude relationship: $k_3 < k_1 < k_2$.

The γ correction circuit 47B performs γ correction processing on the image signals which are outputted from the matrix circuit 47A, on which matrix conversion processing based on the expression (1) shown above has been performed, and which comprise the $R_o$ signal, $G_o$ signal and $B_o$ signal, and outputs the processed image signals.

The image signals outputted from the image processing circuit 47 are converted into analog video signals by the D/A converter 48 and thereafter outputted to the monitor 5.

The above-described sequence of processing is performed in the video processor 4 to display an image of the subject in the narrow band imaging mode on the monitor 5. For example, as an image of the subject in the narrow band imaging mode, images such as those in FIG. 6, i.e., an image in which images of capillaries 101 in the vicinity of a mucosal surface layer in the living body are emphasized, and an image of a residue 102, as an image of a predetermined object different from living tissues, are displayed on the monitor 5. Note that, the residue 102 may be any other predetermined object different from living tissues, e.g., bile or intestinal juice.

The images of capillaries 101 are displayed, for example, in brown or a color close to the brown as a result of the above-described matrix conversion processing performed in the video processor 4. Also, the image of residue 102 is displayed, for example, in magenta or a color close to magenta as a result of the above-described matrix conversion processing performed in the video processor 4. That is, the matrix circuit 47A performs processing in the above-described matrix conversion processing so that the luminance value of the red component and the luminance value of the blue component in the image of residue 102 are substantially equal to each other.

By the above-described function, the endoscopic apparatus 1 in the first embodiment can obtain in narrow band imaging an image in which capillaries in the vicinity of a mucosal surface layer in a living body are emphasized, and can also obtain an image in which an image of a residue has a color different from a red color substantially the same as that of blood. Thus, the endoscopic apparatus 1 in the first embodiment can reduce the burden on an operator or the like in a case where narrow band imaging is performed on a living body.

The matrix circuit 47A in a configuration for obtaining substantially the same effect as that described above is not limited to one for performing matrix conversion processing based on expression (1). For example, the matrix circuit 47A may be configured to perform matrix conversion processing based on an expression (2) shown below.

$$\begin{pmatrix} R_o \\ G_o \\ B_o \end{pmatrix} = \begin{pmatrix} k_1 & 0 \\ 0 & k_2 \\ k_3 & k_4 \end{pmatrix} \begin{pmatrix} Gi \\ Bi \end{pmatrix} \quad (2)$$

The matrix circuit 47A performs matrix conversion processing based on the expression (2) shown above by multiplying the luminance value of the $G_i$ signal read from the memory 46b by $k_1$ to obtain a signal and outputs this signal as an $R_o$ signal which is a red component after the matrix conversion processing.

Also, the matrix circuit 47A performs matrix conversion processing based on the expression (2) shown above by multiplying the luminance value of the $B_i$ signal read from the memory 46c by $k_2$ to obtain a signal and outputs this signal as a $G_o$ signal which is a green component after the matrix conversion processing.

Further, the matrix circuit 47A performs matrix conversion processing based on the expression (2) shown above by multiplying the luminance value of the $G_i$ signal read from the memory 46d by $k_3$ to obtain a signal, multiplying the luminance value of the $B_i$ signal read from the memory 46d by $k_4$ to obtain a signal, and outputs a signal obtained by adding these signals together as a $B_o$ signal which is a blue component after the matrix conversion processing.

Note that, in expression (2), it is noted that the constant $k_3$ is a value larger than the above-described constant $k_3$ and smaller than either of the above-described constant $k_1$ and constant $k_2$. More specifically, it is noted that the values of the constant $k_1$, constant $k_2$, the constant $k_3$ and constant $k_4$ satisfy, for example, a magnitude relationship: $k_3 < k_4 < k_1 < k_2$.

Processing similar to the above-described sequence of processing is performed subsequently in the video processor 4 to display an image of the subject in the narrow band imaging mode on the monitor 5.

When matrix conversion processing based on expression (2) shown above is performed, an image of residue 102 having substantially the same color as that of the image obtained when matrix conversion processing based on expression (1) is performed is displayed on the monitor 5. Also, when matrix conversion processing based on expression (2) shown above is performed, images of capillaries 101 having improved contrast in comparison with those obtained when matrix conversion processing based on expression (1) is performed are displayed on the monitor 5.

When matrix conversion processing based on expression (1) shown above is performed, there is a possibility of an image of a local portion 103, such as shown in FIG. 6, to be displayed on the monitor 5 as an image in a color extremely close to yellow due to a halation. On the other hand, when matrix conversion processing based on expression (2) shown above is performed, an image of a local portion 103, such as shown in FIG. 6, is displayed on the monitor 5 as an image in white or in a color close to white.

The above-described matrix conversion processing based on expression (2) shown above is performed in the matrix circuit 47A to display on the monitor 5 as an image of the subject in the narrow band imaging mode images of capillaries 101 having improved contrast in comparison with those obtained when matrix conversion processing based on expression (1) is performed, an image of a residue 102 having a color different from a red color substantially the same as that of blood, and an image of a local portion 103 in white or in a color close to white.

(Second Embodiment)

Figure 7:
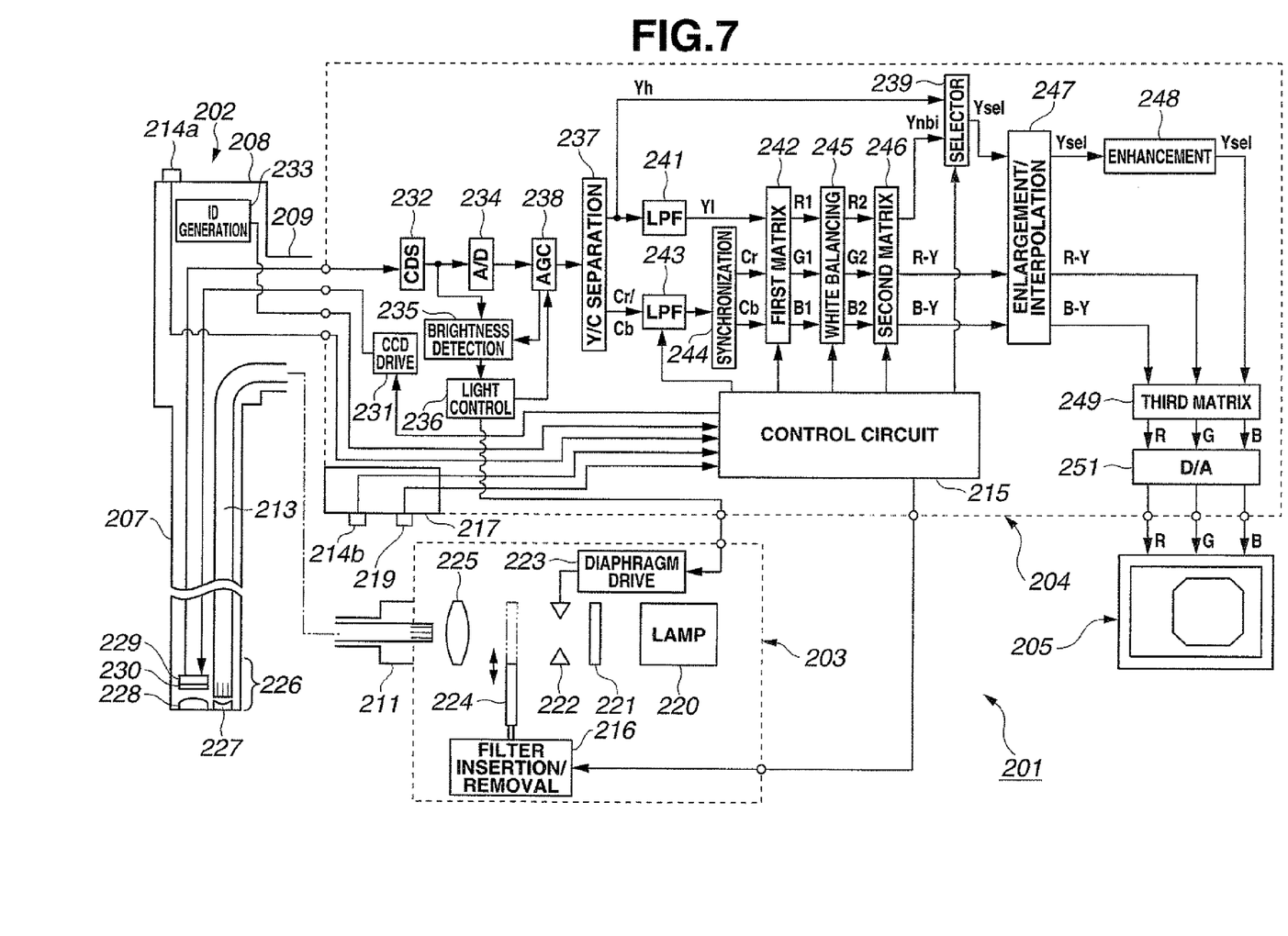
FIG. 7 is a diagram showing an example of a configuration of essential components of an endoscopic apparatus according to a second embodiment.
Figure 8:
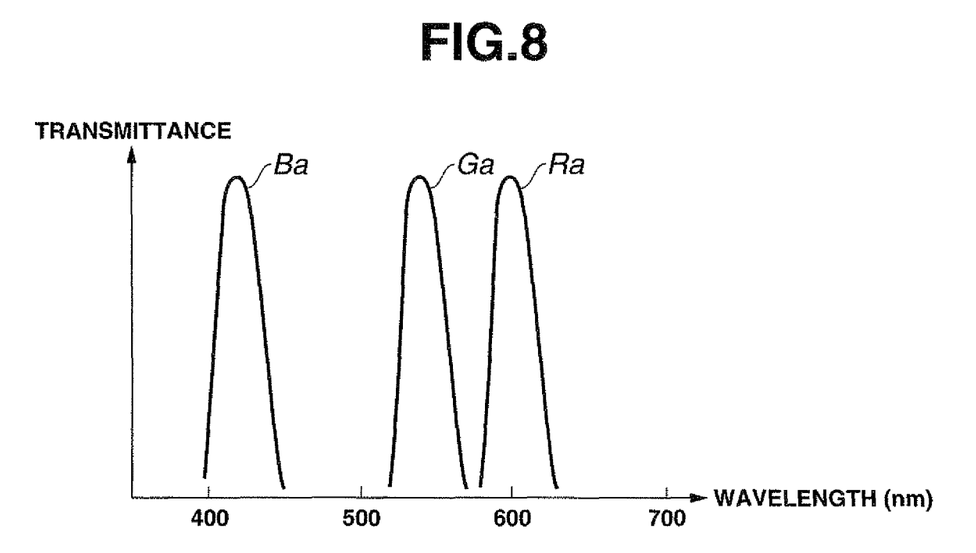
FIG. 8 is a diagram showing an example of spectral characteristics of a narrow band filter provided in the endoscopic apparatus according to the second embodiment.
Figure 9:
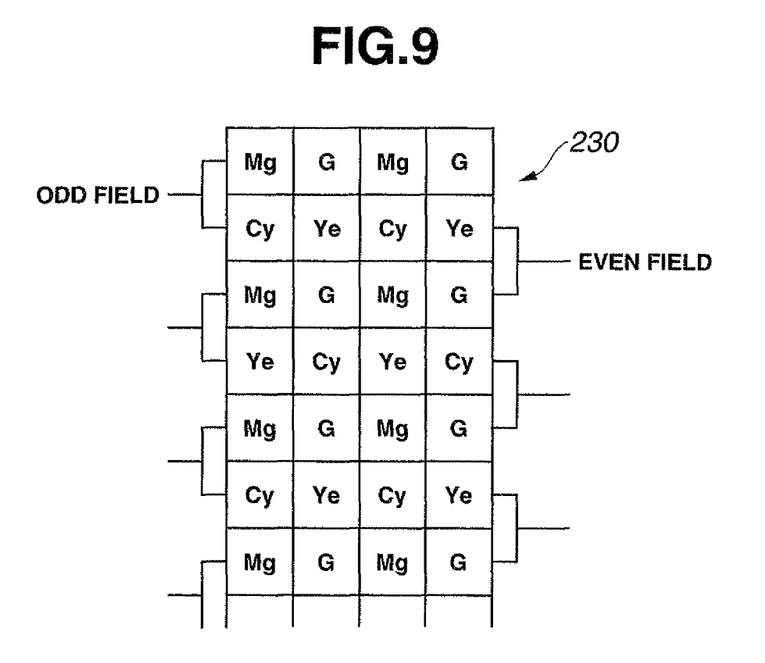
FIG. 9 is a diagram showing an example of arrangement of filters used in a color separating filter provided in the endoscopic apparatus according to the second embodiment.

FIGS. 7 to 9 relate to a second embodiment of the present invention. FIG. 7 is a diagram showing an example of a configuration of essential components of an endoscopic apparatus according to the second embodiment. FIG. 8 is a diagram showing an example of spectral characteristics of a narrow band filter provided in the endoscopic apparatus according to the second embodiment. FIG. 9 is a diagram showing an example of arrangement of filters used in a color separating filter provided in the endoscopic apparatus according to the second embodiment.

In the following description, detailed description will not be made of portions having the same configurations as those in the first embodiment.

The endoscopic apparatus 201 according to the second embodiment has, as its essential components, as shown in FIG. 7, an electronic endoscope (hereinafter referred to simply as "endoscope") 202 inserted in a body cavity or the like to perform endoscopic inspection, a light source device 203 which supplies illumination light to the endoscope 202, a video processor 204 which drives an image pickup unit incorporated in the endoscope 202, and which performs signal processing on signals outputted from the image pickup unit, and a monitor 205 which displays as an endoscopic image an image of a subject picked up by the image pickup unit on the basis of a video signal outputted from the video processor 204.

The endoscope 202 has an elongated insertion portion 207, an operation portion 208 provided on a rear end of the insertion portion 207, and a universal cable 209 extending from the operation portion 208. A light guide connector 211 provided on an end of the universal cable 209 is detachably connected to the light source device 203. Further, the universal cable 209 is detachably connected by a signal connector provided on an end thereof to the video processor 204.

A light guide 213 for transmitting illumination light is inserted in the insertion portion 207. When the light guide connector 211 provided on an end of the light guide 213 on the operator's hand side is connected to the light source device 203, illumination light from the light source device 203 is supplied to the light guide 213.

In a normal imaging mode, the light source device 203 emits white (visible-region) illumination light as normal illumination light and supplies the white illumination light to the light guide 213. In a special imaging mode, e.g., a narrow band imaging mode, the light source device 203 emits narrow band illumination light and supplies the narrow band illumination light to the light guide 213.

A command for changing between the normal imaging mode and the narrow band imaging mode can be provided by operating a mode change switch 214a provided in the operation portion 208 of the endoscope 202. In the endoscopic apparatus 201 according to the second embodiment, the operation to provide a command for changing between the normal imaging mode and the narrow band imaging mode is not limited to operating the mode change switch 214a provided in the endoscope 202. For example, a mode change switch 214b provided in an operating panel 217 of the video processor 204 may be operated to provide the command, or foot switch or a keyboard not illustrated may be operated to provide the command.

A change signal generated by operating the mode change switch 214a or the like is inputted to a control circuit 215 in the video processor 204. This control circuit 215 selectively changes the illumination light supplied from the light source device 203 to the light guide 213 between the normal illumination light and the narrow band illumination light by controlling a filter insertion/removal device 216 according to the change signal.

The control circuit 215 also performs control for changing the characteristics of a video signal processing system in the video processor 204 while interlocking this control with control of changing the illumination light supplied from the light source device 203 to the light guide 213. That is, the video processor 204 can perform signal processings respectively suitable for the normal imaging mode and the narrow band imaging mode by changing the characteristics of the video signal processing system according to the changing command provided by the mode change switch 214a.

The mode change switch 214b and an enhancement level change switch 219 for enhancing the sharpness of an image are also provided in the operating panel 217 of the video processor 204. Signals outputted from the switches 214b and 219 are inputted to the control circuit 215. The mode change switch 214b has the same function as that of the mode change switch 214a.

The light source device 203 incorporates a lamp 220 which emits illumination light including light in a visible region. From the illumination light emitted from the lamp 220, illumination light having substantially the same wavelength band as that of white light is obtained by cutting infrared light with an infrared cutting filter 221, and thereafter enters a diaphragm 222. The amount of opening in the diaphragm 222 is adjusted by control performed by a diaphragm drive circuit 223. A quantity of light according to the amount of opening is permitted to pass through the diaphragm 222.

The filter insertion/removal device 216 configured of a plunger or the like inserts or removes a narrow band filter 224 in the optical path for the illumination light emitted from the lamp 220 (for example, between the diaphragm 222 and a collective lens 225) according to the control of the control circuit 215.

On the other hand, the illumination light passing through the diaphragm 222 enters the collective lens 225 by passing through the narrow band filter 224 (in the narrow band imaging mode) or without passing through the narrow band filter 224 (in the normal imaging mode). After being collected by the collective lens 225, the illumination light is incident on an incidence end surface of the light guide 213 on the operator's hand side.

FIG. 8 is a diagram showing an example of transmittance characteristics of the narrow band filter 224. The narrow band filter 224 exhibits three-peak characteristics and has, for example, narrow band transmission filter characteristic portions Ra, Ga, and Ba for transmission in narrow bands in red, green and blue wavelength regions.

More specifically, the narrow band transmission filter characteristic portions Ra, Ga, and Ba have band-pass characteristics in which the respective center wavelengths are 600 nm, 540 nm and 420 nm and the full widths at half maximum are 20 to 40 nm.

Accordingly, when the narrow band filter 224 is placed on the optical path for the illumination light emitted from the lamp 220, illumination lights which have passed through the narrow band transmission filter characteristic portions Ra, Ga, and Ba in three narrow bands are simultaneously supplied to the light guide 213. On the contrary, when the narrow band filter 224 is not placed on the optical path for the illumination light emitted from the lamp 220, white light (in the visible wavelength region) is supplied to the light guide 213.

The illumination light entering the light guide 213 from the light source device 203 side is transmitted through the light guide 213 and is thereafter emitted to outside through an illumination lens 227 attached to an illumination window provided in a distal end portion 226 of the insertion portion 207, thereby illuminating a surface of a living tissue such as an affected part in a body cavity.

An imaging window is provided in the distal end portion 226 at a position adjacent to the illumination window. An objective lens 228 for forming an optical image by means of return light from a living tissue is mounted in the imaging window. A charge-coupled device (abbreviated as CCD) 229 is disposed as a solid-state image pickup element at the image-forming position of the objective lens 228. The optical image formed by the objective lens 228 is photoelectrically converted by the CCD 229 and thereafter outputted as an image pickup signal.

Complementary color filters shown in FIG. 3, for example, are mounted on a pixel-by-pixel basis on the image pickup surface of the CCD 229 as a color separating filter 230 for optically separating colors.

The complementary color filters have a configuration in which color chips of four colors: magenta (Mg), green (G), cyan (Cy) and yellow (Ye) are disposed in front of CCD elements forming pixels. More specifically, the complementary color filters have a configuration in which Mg and G color chips are alternately disposed in a horizontal direction. The complementary color filters also have a configuration in which a group of color chips repeatedly disposed in order of Mg, Cy, Mg, and Ye, . . . in a vertical direction and another group of color chips repeatedly disposed in order of G, Ye, G, Cy, . . . are alternately disposed.

In the case of the CCD 229 using the complementary color filters as color separating filter 230, pixels in pairs of rows adjacent to each other in the vertical direction are successively read out while being added together. In this reading, the pixels are read by shifting the pairs of rows in correspondence with transition between odd fields and even fields. As is known, a luminance signal and a color signal are produced by processing performed by a Y/C separation circuit 237 in a stage after reading.

The CCD 229 is connected to one end of each of signal lines in the endoscope 202. The signal connector incorporating the other end of each of the signal lines is physically connected to the video processor 204, to establish electrical connections between a CCD drive circuit 231 and a correlative double sampling circuit (CDS circuit) 232 in the video processor 204, and the CCD 229.

Each endoscope 202 has an ID generation section 233 which generates identification information (ID) unique to the endoscope 202. The ID generated in the ID generation section 233 is inputted to the control circuit 215 via the universal cable 209.

The control circuit 215 identifies, on the basis of the input ID, the type of the endoscope 202 connected to the video processor 204, the type of the CCD 229 mounted in the endoscope 202, the number of pixels of the CCD 229 and so on. The control circuit 215 controls the CCD drive circuit 231 so that the CCD 229 in the identified endoscope 202 is in a suitably driven state.

The CCD 229 performs photoelectric conversion of an optical image formed by the objective lens 228 according to a CCD drive signal from the CCD drive circuit 231. The image pickup signal for the optical image photoelectrically converted by the CCD 229 is inputted to the CDS circuit 232.

The image pickup signal inputted to the CDS circuit 232 is outputted to an A/D conversion circuit 234 as a baseband signal from which signal components have been extracted, and is converted into a digital signal by the A/D conversion circuit 234. Simultaneously, the brightness (average luminance of the signal) is detected by a brightness detection circuit 235.

A brightness signal having as information the brightness detected by the brightness detection circuit 235 is inputted to a light control circuit 236 and is thereafter converted into a light control signal having as information a difference from a reference brightness (light control target value). The light control signal is used when the diaphragm drive circuit 223 controls the amount of opening of the diaphragm 222 so that the quantity of illumination light supplied from the light source device 203 to the light guide 213 becomes equal to the quantity of light according to the reference brightness.

The digital signal outputted from the A/D conversion circuit 234 is gain-controlled by an automatic gain control circuit (abbreviated as AGC circuit) 238 so that the signal level becomes equal to a predetermined level), and is thereafter inputted to the Y/C separation circuit 237. The Y/C separation circuit 237 produces a luminance signal Yh (as a color signal C in a broad sense) and line-sequential color difference signals Cr (=2R−G) and Cb (=2B−G) on the basis of the inputted digital signal.

The luminance signal Yh outputted from the Y/C separation circuit 237 is inputted to a selector 239 and also to a first low-pass filter (abbreviated as LPF) 241 which limits a passband for the inputted signal.

The LPF 241 has a wide passband characteristic corresponding to the luminance signal Yh. The luminance signal Yh is filtered according to the passband characteristic to be inputted as a luminance signal Y1 to a first matrix circuit 242.

On the other hand, the color difference signals Cr and Cb are inputted to a (line-sequential) synchronization circuit 244 via a second LPF 243 which limits a passband for the inputted signal.

At this time, a passband characteristic of the second LPF 243 is changed according to the imaging mode by being controlled by the control circuit 215. More specifically, the second LPF 243 is controlled by the control circuit 215 to be set so as to have, in the normal imaging mode, a first passband characteristic in which the passband is lower than that of the first LPF 241. Also, the second LPF 243 is controlled by the control circuit 215 to be set so as to have, in the narrow band imaging mode, a second passband characteristic in which the passband is wider than that in the first passband characteristic and is substantially equal to that of the first LPF 241. The second LPF 243 forms processing characteristic changing means capable of changing a processing characteristic by limiting the passband with respect to the color difference signals Cr and Cb while interlocking with changing of the imaging mode.

The synchronization circuit 244 synchronizes the inputted color difference signals Cr and Cb and outputs these signals to the first matrix circuit 242.

The first matrix circuit 242 produces three primary color signals R1, G1, and B1 according to the luminance signal Y1 and the color difference signals Cr and Cb and outputs the produced three primary color signals R1, G1, and B1 to a white balancing circuit 245.

Also, the first matrix circuit 242 is controlled by the control circuit 215 to change the values of matrix coefficients (determining a conversion characteristic) according to the characteristics of the color separating filter 230 of the CCD 229 and the characteristics of the narrow band filter 224. Thus, the first matrix circuit 242 can produce three primary color signals R1, G1, and B1 without color mixing or by eliminating color mixing substantially completely.

For example, the characteristics of the color separating filter 230 of the CCD 229 incorporated in the endoscope 202 may vary depending on the endoscope 202 actually connected to the video processor 204. The control circuit 215 changes the coefficients in the first matrix circuit 242 according to the characteristics of the color separating filter 230 of the CCD 229 actually used by referring to the ID information. In this way, the video processor 204 can be suitably adapted even to different types of image pickup elements actually used. Thus, the occurrence of a pseudo color can be prevented and three primary color signals R1, G1, and B1 (substantially) free from color mixing can be produced.

Note that, the video processor 204 is capable of producing three primary color signals R1, G1, and B1 free from color mixing and therefore has the function and effect of effectively preventing, particularly in the narrow band imaging mode, the occurrence of a phenomenon in which color signals based on an optical image picked up under narrow band light of a particular color are made not easily discriminable due to color signals based on an optical image picked up under narrow band light of a different color.

The white balancing circuit 245 performs white balancing processing on the inputted three primary color signals R1, G1, and B1 to produce and output three primary color signals R2 G2, and B2.

A second matrix circuit 246 produces and outputs a luminance signal Y and color difference signals R-Y and B-Y on the basis of the three primary color signals R2, 62, and B2 outputted from the white balancing circuit 245.

In the normal imaging mode, in this case, the control circuit 215 sets matrix coefficients in the second matrix circuit 246 as coefficients only enabling generation of the luminance signal Y and the color difference signals R-Y and B-Y from the inputted three primary colors R2, G2, and B2.

In the narrow band imaging mode, the control circuit 215 sets matrix coefficients in the second matrix circuit 246 different from those in the normal imaging mode, as coefficients enabling generation of a luminance signal Ynbi having an increased proportion (weight) with respect to the B signal in particular and the color difference signals R-Y and B-Y from the inputted three primary colors R2, G2, and B2.

A conversion expression in the case of using matrices A and K of three rows and three columns in the cases shown above is as shown by expression (3) below.

$$\begin{pmatrix} Ynbi \\ R-Y \\ B-Y \end{pmatrix} = A * K * \begin{pmatrix} R2 \\ G2 \\ B2 \end{pmatrix} \quad (3)$$

Matrix K may be as shown by expression (4) below, having as its elements the values of the constant $k_1$, the constant $k_2$ and the constant $k_3$ in expression (1) shown above, $$K = \begin{pmatrix} 0 & k_1 & 0 \\ 0 & 0 & k_2 \\ 0 & k_3 & 0 \end{pmatrix} \quad (4)$$

or may be as shown by expression (5) below, having as its elements the values of the constant $k_1$, the constant $k_2$, the constant $k_3$ and the constant $k_4$ in expression (2) shown above.

$$K = \begin{pmatrix} 0 & k_1 & 0 \\ 0 & 0 & k_2 \\ 0 & k_3 & k_4 \end{pmatrix} \quad (5)$$

Matrix A is a matrix for generating a Y color difference signal from RGB signals and uses, for example, known calculation coefficients such as those shown in expression (6) below.

$$A = \begin{pmatrix} 0.299 & 0.587 & 0.114 \\ -0.299 & -0.587 & 0.886 \\ 0.701 & -0.587 & -0.114 \end{pmatrix} \quad (6)$$

The luminance signal Ynbi outputted from the second matrix circuit 246 is inputted to the selector 239. In the normal imaging mode, the selector 239 selects and outputs the luminance signal Yh under the control of the control circuit 215. In the narrow band imaging mode, the selector 239 selects and outputs the luminance signal Ynbi under the control of the control circuit 215. Note that, in FIG. 7, the luminance signal Yh or Ynbi selectively outputted from the selector 239 is shown as luminance signal Ysel.

The color difference signals R-Y and B-Y outputted from the second matrix circuit 246 are inputted to an enlargement/interpolation circuit 247 together with the luminance signal Ysel (luminance signal Yh or Ynbi) outputted via the selector 239.

The luminance signal Ysel undergoes enlargement processing in the enlargement/interpolation circuit 247 and sharpness enhancement processing in an enhancement circuit 248 and is thereafter inputted to a third matrix circuit 249. The color difference signals R-Y and B-Y having undergone enlargement processing in the enlargement/interpolation circuit 247 is also inputted to the third matrix circuit 249.

The luminance signal Ysel and the color difference signals R-Y and B-Y undergo processing for conversion into three primary color signals R, G, and B in the third matrix circuit 249 and D/A conversion processing in a D/A conversion circuit 251 and is thereafter outputted from a video signal output end of the video processor 204 to the monitor 205.

The control circuit 215 changes and sets the characteristic of the LPF 243, the matrix coefficients in the first matrix circuit 242 and the matrix coefficients in the second matrix circuit 246 and selects the luminance signal Yh/Ynbi in the selector 239 according to change or selection of the imaging mode made by operating the mode change switch 214a or 214b.

The control circuit 215 also controls the operation of the filter insertion/removal device 216 in the light source device 203 according to change of the imaging mode. Also, the control circuit 215 makes a gain setting in the white balancing circuit 245 at the time of white balancing.

Description will next be made of the operation of the endoscopic apparatus 201 according to the present embodiment.

An operator or the like first powers on the components of the endoscopic apparatus 201, i.e., the endoscope 202, the light source device 203, the video processor 204 and the monitor 205 to activate the components. It is assumed that, in the activated state, the endoscope 202, the light source device 203 and the video processor 204 are set in the normal imaging mode.

When detecting change of the imaging mode of the video processor 204 from the normal imaging mode to the narrow band imaging mode on the basis of the imaging mode change signal outputted from the mode change switch 214a or 214b, the control circuit 215 performs control for inserting the narrow band filter 224 on the optical path of the lamp 220 on the filter insertion/removal device 216. The control circuit 215 also performs control according to the narrow band imaging mode on the selector 239, the first matrix circuit 242, the second LPF 243, the white balancing circuit 245 and the second matrix circuit 246 on the basis of the imaging mode change signal outputted from the mode change switch 214a or 214b.

On the other hand, the light source device 203 supplies narrow band illumination light according to the transmission characteristics of the narrow band filter 224 to the light guide 213 under the control of the control circuit 215.

The narrow band illumination light supplied from the light source device 203 is emitted to the outside through the light guide 213 and the illumination lens 227 to illuminate a surface of a living tissue such as an affected part in a body cavity.

An image of the subject illuminated with the narrow band illumination light is formed by the objective lens 228, optically color-separated by the color separating filter 230, picked-up by the CCD 229 and thereafter outputted as an image pickup signal to the video processor 204.

The image pickup signal outputted to the video processor 204 has the signal components thereof extracted by the CDS circuit 232 and is converted into a digital signal by the A/D conversion circuit 234, gain-controlled by the AGC circuit 238 and thereafter inputted to the Y/C separation circuit 237.

The Y/C separation circuit 237 produces the luminance signal Yh and the color difference signals Cr and Cb on the basis of the inputted digital signal. The Y/C separation circuit 237 outputs the luminance signal Yh to the selector 239 and to the first LPF 241 and outputs the color difference signals Cr and Cb to the second LPF 243.

The luminance signal Yh undergoes filtering processing in the first LPF 241 and is thereafter outputted as luminance signal Y1 to the first matrix circuit 242. The color difference signals Cr and Cb undergo filtering processing based on the (above-described) second passband characteristic of the second LPF 243, synchronized by the synchronization circuit 244 and thereafter outputted to the first matrix circuit 242.

The first matrix circuit 242 produces three primary color signals R1, G1, and B1 according to the inputted luminance signal Y1 and color difference signals Cr and Cb, and outputs the produced three primary color signals R1, G1, and B1 to the white balancing circuit 245.

The white balancing circuit 245 produces three primary color signals R2, G2, and B2 by performing white balancing processing on the inputted three primary color signals R1, G1, and B1, and outputs the three primary color signals R2, G2, and B2 to the second matrix circuit 246.

The second matrix circuit 246 produces the luminance signal Ynbi and the color difference signals R-Y and B-Y by performing conversion processing based on expressions (3), (4), and (6) shown above on the inputted three primary color signals R2, G2, and B2. The second matrix circuit 246 outputs the luminance signal Ynbi to the selector 239 and outputs the color difference signals R-Y and B-Y to the enlargement/interpolation circuit 247.

The selector 239 selects the luminance signal Ynbi under the control of the control circuit 215 and outputs the luminance signal Ynbi as luminance signal Ysel to the enlargement/interpolation circuit 247.

The luminance signal Ysel undergoes enlargement processing in the enlargement/interpolation circuit 247 and sharpness enhancement processing in the enhancement circuit 248 and is thereafter inputted to the third matrix circuit 249. The color difference signals R-Y and B-Y having undergone enlargement processing in the enlargement/interpolation circuit 247 is inputted to the third matrix circuit 249.

The luminance signal Ysel and the color difference signals R-Y and B-Y undergo processing for conversion into three primary color signals R, G, and B in the third matrix circuit 249, undergo the D/A conversion processing in the D/A conversion circuit 251 and are thereafter outputted from the video signal output end of the video processor 204 to the monitor 205.

The above-described sequence of processing is performed in the video processor 204 to display an image of the subject in the narrow band imaging mode on the monitor 205. For example, as an image of the subject in the narrow band imaging mode, images such as those in FIG. 6, i.e., an image in which images of capillaries 101 in the vicinity of a mucosal surface layer in the living body are emphasized, and an image of a residue 102, as an image of a predetermined object different from living tissues, are displayed on the monitor 205. Note that, the residue 102 may be any other predetermined object different from living tissues, e.g., bile or intestinal juice.

The images of capillaries 101 are displayed, for example, in brown or a color close to the brown as a result of the above-described matrix conversion processing performed in the video processor 204. Also, the image of residue 102 is displayed, for example, in magenta or a color close to the magenta as a result of the above-described matrix conversion processing performed in the video processor 204. That is, the second matrix circuit 246 performs processing in the above-described matrix conversion processing so that the luminance value of the red component and the luminance value of the blue component in the image of residue 102 are substantially equal to each other.

By the above-described working, the endoscopic apparatus 201 in the second embodiment can obtain in narrow band imaging an image in which capillaries in the vicinity of a mucosal surface layer in a living body are emphasized, and can also obtain an image in which an image of a residue has a color different from a red color substantially the same as that of blood. Thus, the endoscopic apparatus 201 in the second embodiment can reduce the burden on an operator or the like in a case where narrow band imaging is performed on a living body.

The second matrix circuit 246 may perform conversion processing based on expression (3), expression (5) and expression (6) shown above to obtain an effect similar to the above-described effect.

When matrix conversion processing based on expression (3), expression (5) and expression (6) shown above is performed, an image of residue 102 having substantially the same color as that of the image obtained when matrix conversion processing based on expression (3), expression (4) and expression (6) shown above is performed is displayed on the monitor 205. Also, when matrix conversion processing based on expression (3), expression (5) and expression (6) shown above is performed, images of capillaries 101 having improved contrast in comparison with those obtained when matrix conversion processing based on expression (3), expression (4) and expression (6) is performed are displayed on the monitor 205.

When matrix conversion processing based on expression (3), expression (4) and expression (6) shown above is performed, there is a possibility of an image of a local portion 103, such as shown in FIG. 6, to be displayed on the monitor 205 as an image in a color extremely close to yellow due to a halation. On the other hand, when matrix conversion processing based on expression (3), expression (5) and expression (6) shown above is performed, an image of a local portion 103, such as shown in FIG. 6, is displayed on the monitor 205 as an image in white or in a color close to white.

The above-described matrix conversion processing based on expression (3), expression (5) and expression (6) shown above is performed in the second matrix circuit 246 to display on the monitor 205 images of capillaries 101 having improved contrast in comparison with those obtained when matrix conversion processing based on expression (3), expression (4) and expression (6) is performed, an image of a residue 102 having a color different from a red color substantially the same as that of blood, and an image of a local portion 103 in white or in a color close to white.

Needless to say, the present invention is not limited to the above-described embodiments. Various changes and applications may be made without departing from the scope of the present invention.

What is claimed is:

1. An endoscopic apparatus comprising:
a mode selecting unit capable of selecting:
   a normal imaging mode, and
   a narrow band imaging mode for obtaining an image in which blood vessels in a mucosal surface layer in a living body are emphasized;
an illumination unit configured to simultaneously emit to a subject in a living body first narrow band light having a wavelength band in a blue region and second narrow band light having a wavelength band in a green region, when the narrow band imaging mode is selected in the mode selecting unit;
an image pickup unit configured to:
   receive reflected light from the subject illuminated with the first narrow band light and reflected light from the subject illuminated with the second narrow band light, and
   output the received light as an image pickup signal;
a luminance color difference conversion unit configured to generate a first luminance signal and a first color difference signal from the image pickup signal outputted from the image pickup unit;
a first signal conversion unit configured to generate a first three primary color signal having a red component, a green component and a blue component from the first luminance signal and the first color difference signal generated by the luminance color difference conversion unit; and
a color tone conversion unit configured to generate a signal to be displayed on a display unit based on a first multiplication result of multiplying the green component generated by the first signal conversion unit by a first coefficient, a second multiplication result of multiplying the green component by a second coefficient, and a third multiplication result of multiplying the blue component generated by the first signal conversion unit by a third coefficient, when the narrow band imaging mode is selected in the mode selecting unit,
wherein the color tone conversion unit, when the narrow band imaging mode is selected in the mode selecting unit, is configured to set the first coefficient, the second coefficient and the third coefficient such that the red component and the blue component have a substantially equal luminance value in the signal to be displayed on the display unit, thereby causing at least one of a residue, bile and intestinal juice existing in the living body, which have been obtained as the image, to be displayed on the display unit in a color other than a red color, and causing blood vessels of the subject to be emphasized and displayed on the display unit.

2. The endoscopic apparatus according to claim 1, wherein the illumination unit successively emits the first narrow band light and the second narrow band light to the subject.

3. The endoscopic apparatus according to claim 1, wherein the color tone conversion unit generates a second luminance signal and a second color difference signal as signals to be displayed on the display unit.

4. The endoscopic apparatus according to claim 3, further comprising a second signal conversion unit configured to generate a second three primary color signal having a second red component, a second green component and a second blue component from the second luminance signal and the second color difference signal, and output the generated second three primary color signal.

5. The endoscopic apparatus according to claim 3 wherein the second coefficient is smaller than the first coefficient and the first coefficient is small than the third coefficient.

6. The endoscopic apparatus according to claim 1, wherein the second coefficient is smaller than the first coefficient.

7. The endoscopic apparatus according to claim 1, wherein the color other than the red color is magenta.

8. The endoscopic apparatus according to claim 1, wherein the first narrow band light is blue light whose center wavelength is 415 nm, and the second narrow band light is green light whose center wavelength is 540 nm.

9. An endoscopic apparatus comprising:
a mode selecting unit capable of selecting:
   a normal imaging mode, and
   a narrow band imaging mode for obtaining an image in which blood vessels in a mucosal surface layer in a living body are emphasized;
an illumination unit configured to simultaneously emit to a subject in a living body first narrow band light having a wavelength band in a blue region and second narrow band light having a wavelength band in a green region, when the narrow band imaging mode is selected in the mode selecting unit;
an image pickup unit configured to:
   receive reflected light from the subject illuminated with the first narrow band light and reflected light from the subject illuminated with the second narrow band light, and output the received light as an image pickup signal;

a luminance color difference conversion unit configured to generate a first luminance signal and a first color difference signal from the image pickup signal outputted from the image pickup unit;

a first signal conversion unit configured to generate a first three primary color signal having a red component, a green component and a blue component from the first luminance signal and the first color difference signal generated by the luminance color difference conversion unit; and a color tone conversion unit configured to generate a signal to be displayed on a display unit based on a first multiplication result of multiplying the green component generated by the first signal conversion unit by a first coefficient, a second multiplication result of adding a result of multiplying the green component by a second coefficient and a result of multiplying the blue component by a third coefficient, and a third multiplication result of multiplying the blue component by a fourth coefficient, when the narrow band imaging mode is selected in the mode selecting unit, wherein the color tone conversion unit, when the narrow band imaging mode is selected in the mode selecting unit, sets the first coefficient, the second coefficient, the third coefficient, and the fourth coefficient such that the red component and the blue component have a substantially equal luminance value in the signal to be displayed on the display unit, thereby causing at least one of a residue, bile and intestinal juice existing in the living body, which have been obtained as the image, to be displayed on the display unit in a color other than a red color, and causing the blood vessels of the subject to be emphasized and displayed on the display unit.

10. The endoscopic apparatus according to claim 9, wherein the color tone conversion unit generates a second luminance signal and a second color difference signal as signals to be displayed on the display unit.

11. The endoscopic apparatus according to claim 10, further comprising a second signal conversion unit configured to generate a second three primary color signal having a second red component, a second green component and a second blue component from the second luminance signal and the second color difference signal, and output the generated second three primary color signal.

12. The endoscopic apparatus according to claim 9, wherein the second coefficient is smaller than the first coefficient and the third coefficient.

13. The endoscopic apparatus according to claim 9, wherein the second coefficient is smaller than the third coefficient, the third coefficient is smaller than the first coefficient, and the first coefficient is smaller than the fourth coefficient.

14. The endoscopic apparatus according to claim 9 wherein the color other than the red color is magenta.

15. The endoscopic apparatus according to claim 9, wherein the first narrow band light is blue light whose center wavelength is 415 nm, and the second narrow band light is green light whose center wavelength is 540 nm.

* * * * *